US007641852B1

(12) United States Patent
McPhail et al.

(10) Patent No.: US 7,641,852 B1
(45) Date of Patent: Jan. 5, 2010

(54) STERILIZER WITH VACUUM-ASSISTED AIR REMOVAL

(75) Inventors: Neil McPhail, Vancouver (CA); Darko Vilotijevic, Toronto (CA); Dorin Cioraca, Toronto (CA); Eduardo C. Ghelman, Etobicoke (CA); Edward House, Toronto (CA); William Stefanuk, Waterloo (CA); Winston L Zeng, Raleigh, NC (US)

(73) Assignee: Scican Ltd., Toronto, Ontario (CA)

( * ) Notice: Subject to any disclaimer, the term of this patent is extended or adjusted under 35 U.S.C. 154(b) by 0 days.

(21) Appl. No.: 09/958,035

(22) PCT Filed: Apr. 6, 2000

(86) PCT No.: PCT/CA00/00377

§ 371 (c)(1),
(2), (4) Date: Jun. 18, 2003

(87) PCT Pub. No.: WO00/59553

PCT Pub. Date: Oct. 12, 2000

(30) Foreign Application Priority Data

Apr. 6, 1999 (CA) .................................. 2268042

(51) Int. Cl.
*A61L 2/08* (2006.01)
(52) U.S. Cl. .................. 422/26; 422/295; 422/297; 422/28; 422/33; 237/67
(58) Field of Classification Search .................. 422/26, 422/295, 297, 300, 28, 33; 237/67
See application file for complete search history.

(56) References Cited

U.S. PATENT DOCUMENTS 1,746,522 A * 2/1930 Carleton ..................... 392/485

| | | | | | |
|---|---|---|---|---|---|
| 2,258,746 | A | * | 10/1941 | Dickman | ..................... 122/39 |
| 2,868,616 | A | * | 1/1959 | Poitras | ..................... 422/25 |
| 3,086,263 | A | * | 4/1963 | Huber | ..................... 422/116 |
| 3,834,872 | A | | 9/1974 | Joslyn | |
| 4,105,407 | A | * | 8/1978 | Sanderson | ..................... 422/26 |
| 4,759,909 | A | * | 7/1988 | Joslyn | ..................... 422/26 |
| 5,145,642 | A | | 9/1992 | Feathers, III et al. | |

(Continued)

FOREIGN PATENT DOCUMENTS

CA 2268042 10/2000

(Continued)

OTHER PUBLICATIONS

"Steam Generator", IBM Technical Disclosure Bulletin (NN73053887), Published May 1973, vol. 15, Issue 12, p. 3887.*

*Primary Examiner*—Sean E Conley
(74) *Attorney, Agent, or Firm*—Clark & Brody (57) ABSTRACT

A sterilizer for medical instruments is compact and designed to be placed on a table top. The sterilizer provides includes a cavity for receiving a cassette holding the instruments to be sterilized. A stream circuit provides steam to the cassette for sterilization, and the time required for sterilization is reduced by withdrawing air from the cassette by application of a vacuum. The cavity is evacuated at the same time as the cassette to prevent application of high stresses to the cassette during the vacuum-assisted withdrawal of air. The time for sterilization is further reduced by use of dual heat exchangers to reduce the volume removed from the cassette.

19 Claims, 9 Drawing Sheets

U.S. PATENT DOCUMENTS

| | | | |
|---|---|---|---|
| 5,160,700 A * | 11/1992 | Anderson et al. | 422/34 |
| 5,207,237 A | 5/1993 | Langford | |
| 5,271,893 A | 12/1993 | Newman | |
| 5,290,511 A | 3/1994 | Newman | |
| 5,310,524 A | 5/1994 | Campbell | |
| 5,368,821 A | 11/1994 | Schmoegner et al. | |
| 5,533,539 A * | 7/1996 | Sutter et al. | 134/95.2 |
| 5,543,119 A | 8/1996 | Sutter et al. | |
| 5,571,476 A * | 11/1996 | Newman | 422/26 |
| 5,759,502 A | 6/1998 | Spencer | |
| 5,993,754 A | 11/1999 | Lemmen | |
| 6,010,670 A | 1/2000 | Berry, Jr. | |
| 6,066,294 A * | 5/2000 | Lin et al. | 422/28 |

FOREIGN PATENT DOCUMENTS

| | | |
|---|---|---|
| DE | 197 14 298 | 10/1998 |
| JP | 8-508663 | 9/1996 |

* cited by examiner

STERILIZER WITH VACUUM-ASSISTED AIR REMOVAL

TECHNICAL FIELD

This invention relates to the art of automated sterilizers. In particular, the invention relates to an automated sterilizer designed particularly for sterilizing medical and dental instruments.

BACKGROUND

Sterilizers for medical instruments in the prior art may be large, such as sterilizers used in hospitals, or smaller, such as sterilizers designed for use in a dentist's office and to fit easily on a table. An example of the latter type is that shown in U.S. Pat. No. 5,271,893 (Newman).

The requirements for sterilizing medical instruments are generally prescribed by governing authorities. Thus, the challenge has been to provide an affordable apparatus capable of automatically carrying out the prescribed procedure in the shortest time period. One requirement is that the instrument to be sterilized be subjected to saturated steam at a prescribed temperature for a prescribed period of time. Thus, the interior volume of the sterilizer must be filled with saturated steam, which requires the air in the sterilizer to be replaced with saturated steam as quickly as possible.

The system shown in U.S. Pat. No. 5,271,893 relies on channeling incoming steam to one end of a cassette while allowing air to flow out the other end to purge the air and replace it completely with the steam.

SUMMARY OF THE INVENTION

A desktop sterilizer in accordance with the invention implements a prescribed sterilizing protocol quickly and efficiently. The system provides an armature of extruded aluminum that forms an enclosure for a portable cassette. The walls of the armature include a plurality of cavities that are separated by webbing for rendering the walls thermally insulating, highly resistant to deflection during pressurization, and light. The removable cassette may be of various kinds and is preferably that described in Canadian Patent Application 2,268,042.

The system further includes a steam generator for generating steam by spraying water droplets onto a spiral heating element. The supply of water to the steam generator is controlled as a function of the temperature of the heating element, and the steam generator is oriented to accentuate the changes to increase the sensitivity of the temperature measurement.

The armature is connected to a vacuum pump and to the steam generator, whose operation is controlled such that the cassette can be evacuated by vacuum and then supplied with saturated steam in accordance with a process that effectively and efficiently complies with the prescribed sterilization protocol. Because the armature is evacuated in the preferred process, the sterilizer can be subjected to vacuum and yet be of a design that allows inexpensive manufacture.

BRIEF DESCRIPTION OF THE DRAWINGS

FIG. 7b is a vertical cross section of the nozzle shown in FIG. 7a.

DETAILED DESCRIPTION OF THE PREFERRED EMBODIMENT

Figure 1:
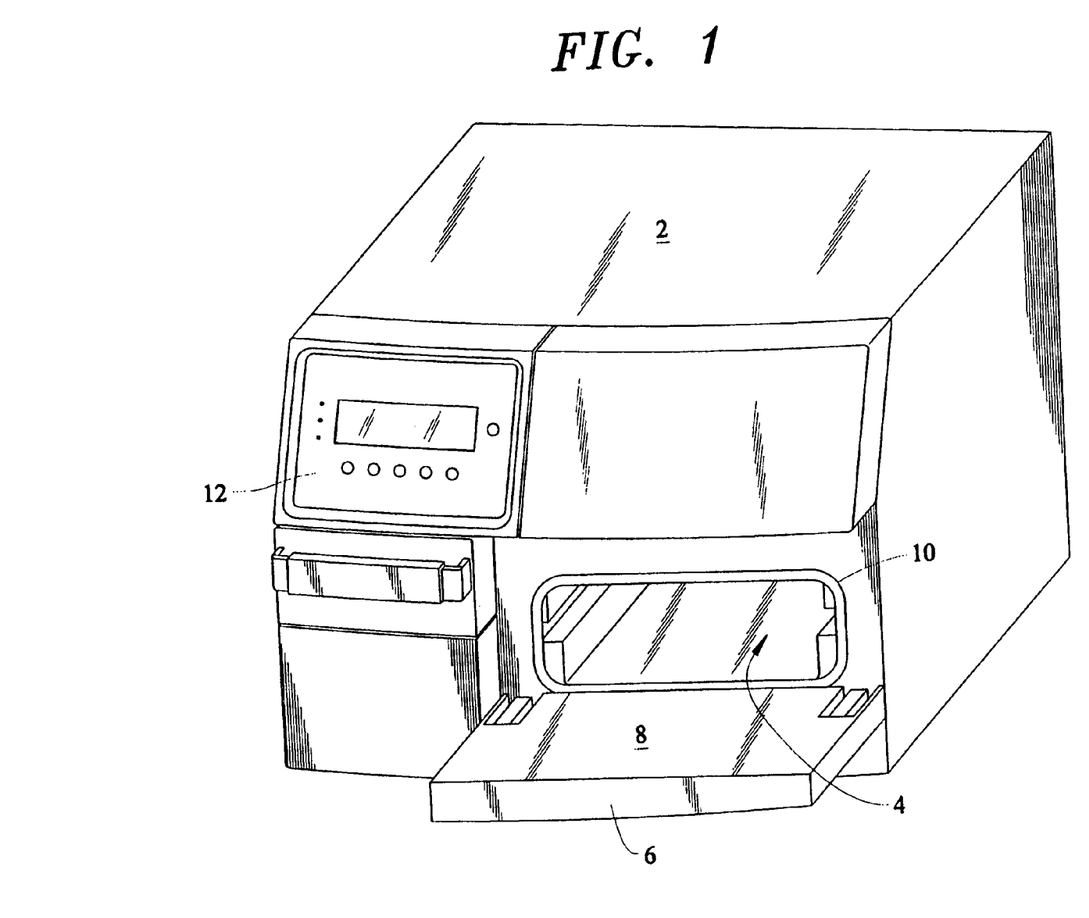
FIG. 1 is a perspective of a sterilizer in accordance with the invention.

With reference to FIG. 1, a sterilizer in accordance with the invention comprises a housing 2 for supporting a plurality of elements, as will be explained in detail below. The sterilizer is designed to be relatively small, e.g., able to fit on a table top in a doctor or dentist's office. The sterilizer as shown holds only one cassette, but it could be designed to hold more than one cassette. The cassettes receive instruments to be sterilized and are preferably made of relatively thin metal to reduce cost and weight.

The sterilizer provides at least one cavity 4 for receiving a cassette, and a door 6 allows access to the cavity. The door is preferably mounted with known hinge structure in such a manner that when in the open position shown its inner surface 8 is flush with the bottom surface of the cavity. This arrangement facilitates insertion and removal of the cassette. The perimeter of the cavity opening is further provided with a seal 10 to allow a vacuum to be drawn in the cavity 4, as will be described further below. A display 12 is provided to communicate various aspects of the process to an operator.

Figure 2:
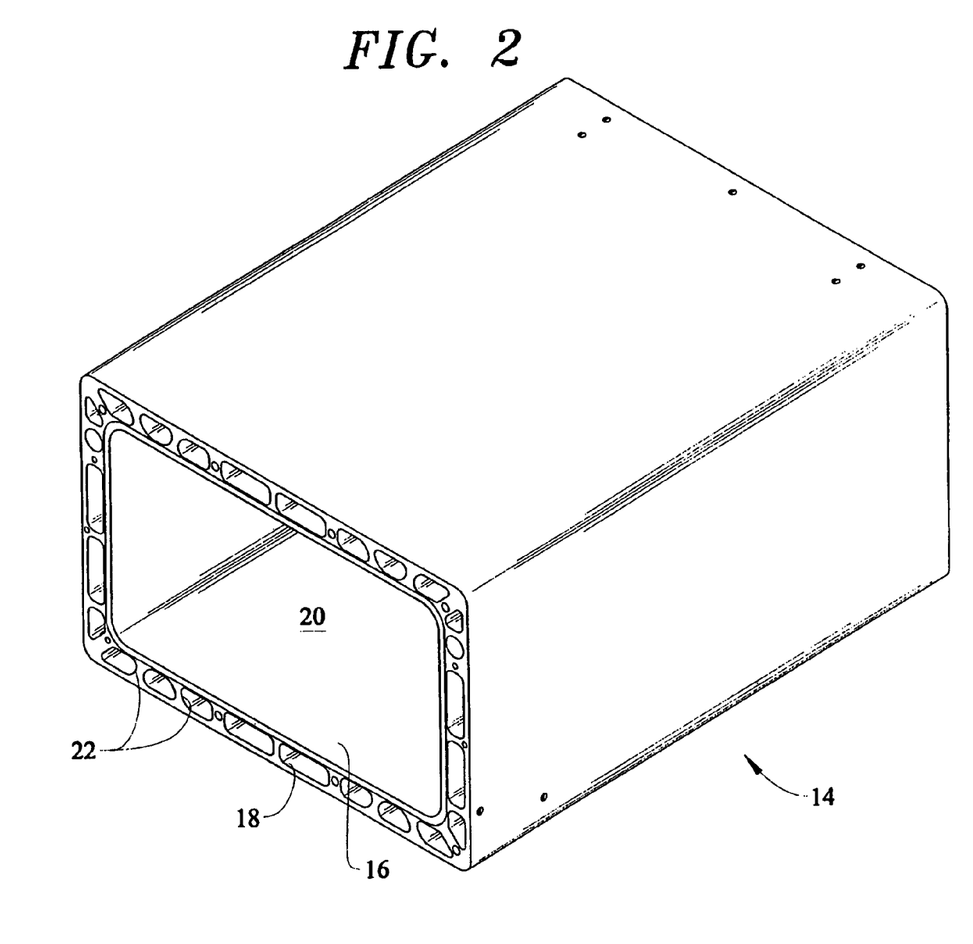
FIG. 2 is a perspective of an armature element of the sterilizer shown in FIG. 1.

A preferred armature component of the sterilizer will be described with reference to FIG. 2.

Traditional steam sterilizers use a cylindrical pressure vessel to receive both the load to be sterilized, such as medical instruments, and the steam sterilant. Because the steam must be maintained at a significant pressure to reach the temperatures required for effective sterilization, it generates a large force on the walls of the pressure vessel. The sterilization vessel must be capable of withstanding this force with minimal deflection to ensure proper operation of the seals. If the vessel distorts too much, the seals will be ineffective, and steam will leak from the vessel. Of course, the vessel must also be capable of accommodating the overall stresses provided by the forces of pressurization.

In the cassette autoclave of the invention, the steam sterilant containment and force containment functions are provided by two separate components. A cassette provides the steam containment function, while an armature 14, as shown in FIG. 2, provides force containment. To provide efficient use of space for storage of instruments by the cassette, the cassette and, hence, the armature are preferably rectangular in cross section.

Previous embodiments of the armature (e.g., that used in U.S. Pat. No. 5,271,893) consisted of welded steel plates that were painted for corrosion protection. This armature was heavy and required extensive testing to prove that the welds were sound. Further, the prior armature was not designed to be pressure tight because the cassette contained the steam and was not subjected to vacuum draws.

The armature 14 of the present invention is, however, simple to fabricate, lighter, more accurate in dimensions, and less expensive than the prior armature. Further, while the armature 14 can be used for the conventional cassette sterilizer described in the '893 patent, it is particularly useful in the present invention because it is pressure tight to permit vacuum withdrawal of the cavity receiving the cassette.

The armature 14 is an extruded profile comprising two spaced walls 16 and 18, with the wall 16 forming an enclosure 20. The walls are connected by a series of ribs 22, or webs, which are sized and located such that the two walls and the ribs carry the stresses efficiently. The webs and double wall serve to increase the section modulus of the structure, therefore increasing bending stiffness (decreasing deflection) without substantially increasing weight.

The webs also allow circulation of cooling or heating fluid (air, water, steam, hydraulic fluid, and oil) between the walls provided that the extrusion is fixed to a suitable manifold (not shown). Also, because the armature is extruded the inner wall is pressure tight and can be made easily of any length.

The cross section of the extrusion is shown to be rectangular, but it is not limited to any particular shape. Preferably, the cross section suits the cassette size and shape and can be rectangular, square, round, elliptical or any other shape. The armature material may be aluminum, magnesium, titanium or any other material that can be extruded. In the preferred sterilizer of FIG. 1, the armature is of aluminum.

Figure 3:
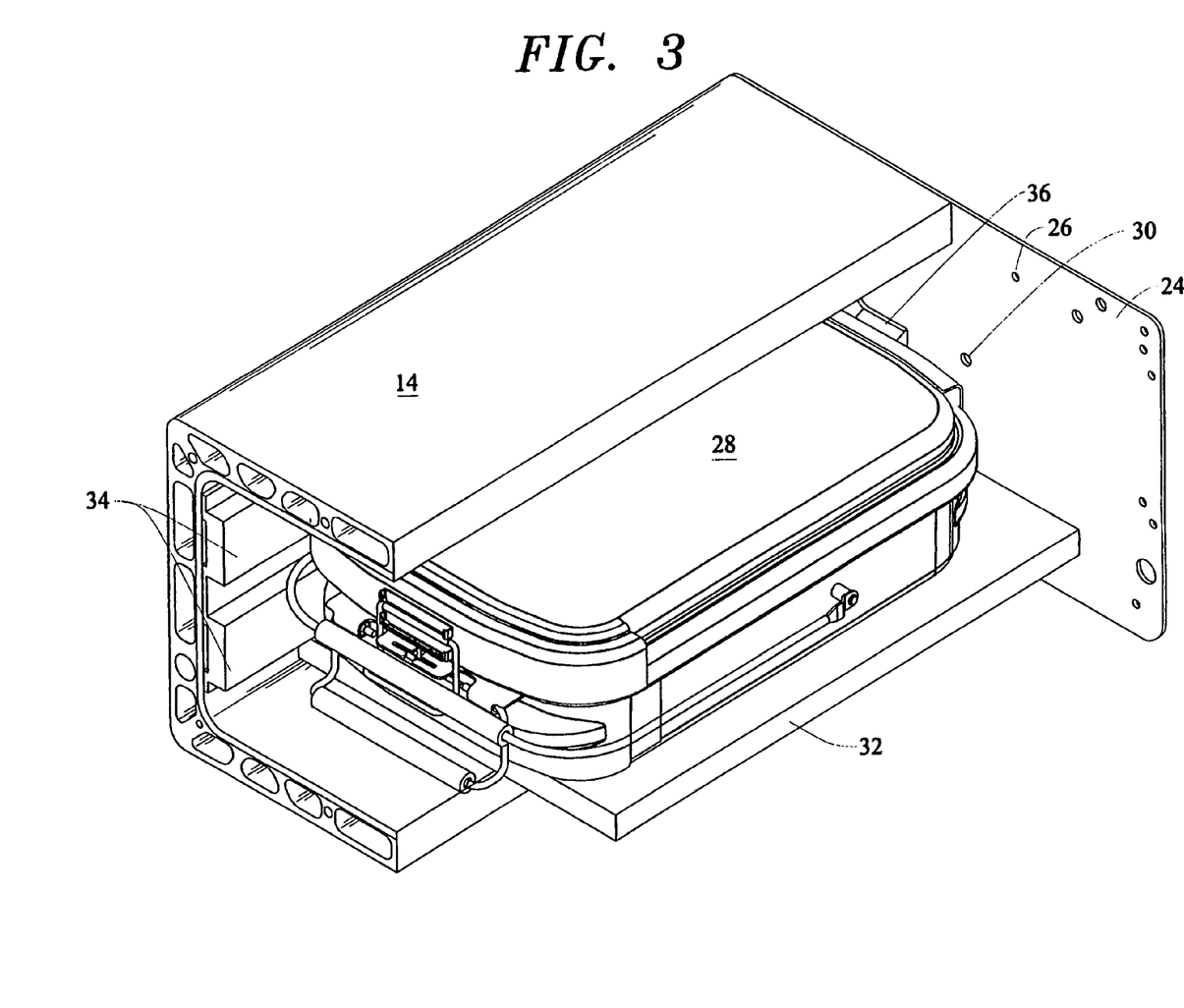
FIG. 3 is a cut away showing the armature of the sterilizer of FIG. 1 supporting a cassette.

FIG. 3 shows further details of the structure of the preferred sterilizer for supporting a cassette 28. The armature 14 is mounted in the sterilizer housing by various brackets that are not shown. A rear plate 24 is secured to the rear of the armature by bolts (not shown) passing through holes 26, and the armature is attached to the housing. The armature 14 is sealed to the rear plate, as by a gasket (not shown), to provide a sealed cavity when the door 6 is closed against seal 10. The cavity of the preferred sterilizer is not subjected to positive gauge pressure, which means that the door and rear plate need not be able to withstand outward forces. The cavity of the sterilizer is evacuated through opening 30 during evacuation phases, as will be described below and, therefore, subjected to vacuum pressure. Thus, the door and rear plate are subjected only to negative gauge pressures.

The door 6 is designed to be capable of withstanding negative atmosphere, and because the door is held against the seal 10 during evacuation of the cavity 4 by pressure from the exterior, the primary requirement is that the door will not buckle under the forces generated by that pressure.

Heating the cassette is necessary during the sterilization cycle, and electric heating plates 32, which are placed, respectively, between the upper and lower surfaces of the cassette and the armature, provide this.

During the sterilization phase, steam supplied to the cassette generates positive pressure. The cassette 28 is made of lightweight material, however, and cannot withstand this large pressure differential. Thus, the cavity is designed such that the armature 14 resists the force generated by this pressure.

The pressures on the upper and lower surfaces of the cassettes are transmitted to the armature by the heating plates 32, the pressures on the sides of the cassette are transmitted to the armature by the isolation plates 34, and the pressure on the back of the cassette is transmitted to the armature by the rear isolation plate 36. The isolation plates are arranged on the sides of the cavity to engage the cassette or reinforcing bumpers on the cassette, and the rear plate supports a rear isolation plate for engaging a rear bumper of the cassette.

It will be appreciated from the structure described that a cassette, such as that described in the mentioned Canadian patent application, is easily inserted in the cavity by opening the door and sliding it inwardly. Insertion of the cassette engages valves on the cassette with probes (not shown) supported on the rear plate to connect the interior of the cassette with the steam system to be described below. Also, a magnetic reed switch, which is part of the control circuitry, senses insertion of the cassette.

Figure 4:
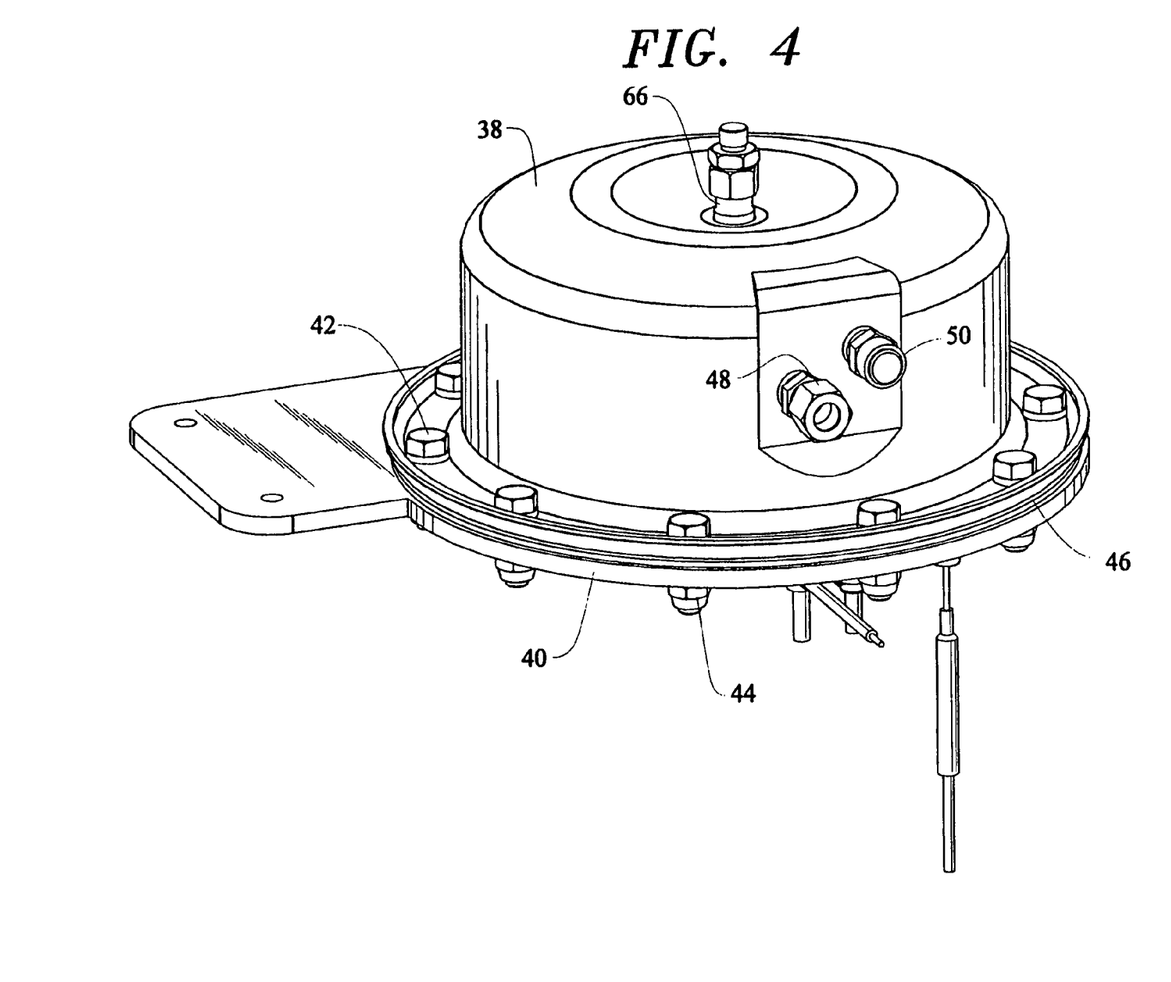
FIG. 4 is a perspective view of a steam generator element of the sterilizer of FIG. 1.
Figure 5:
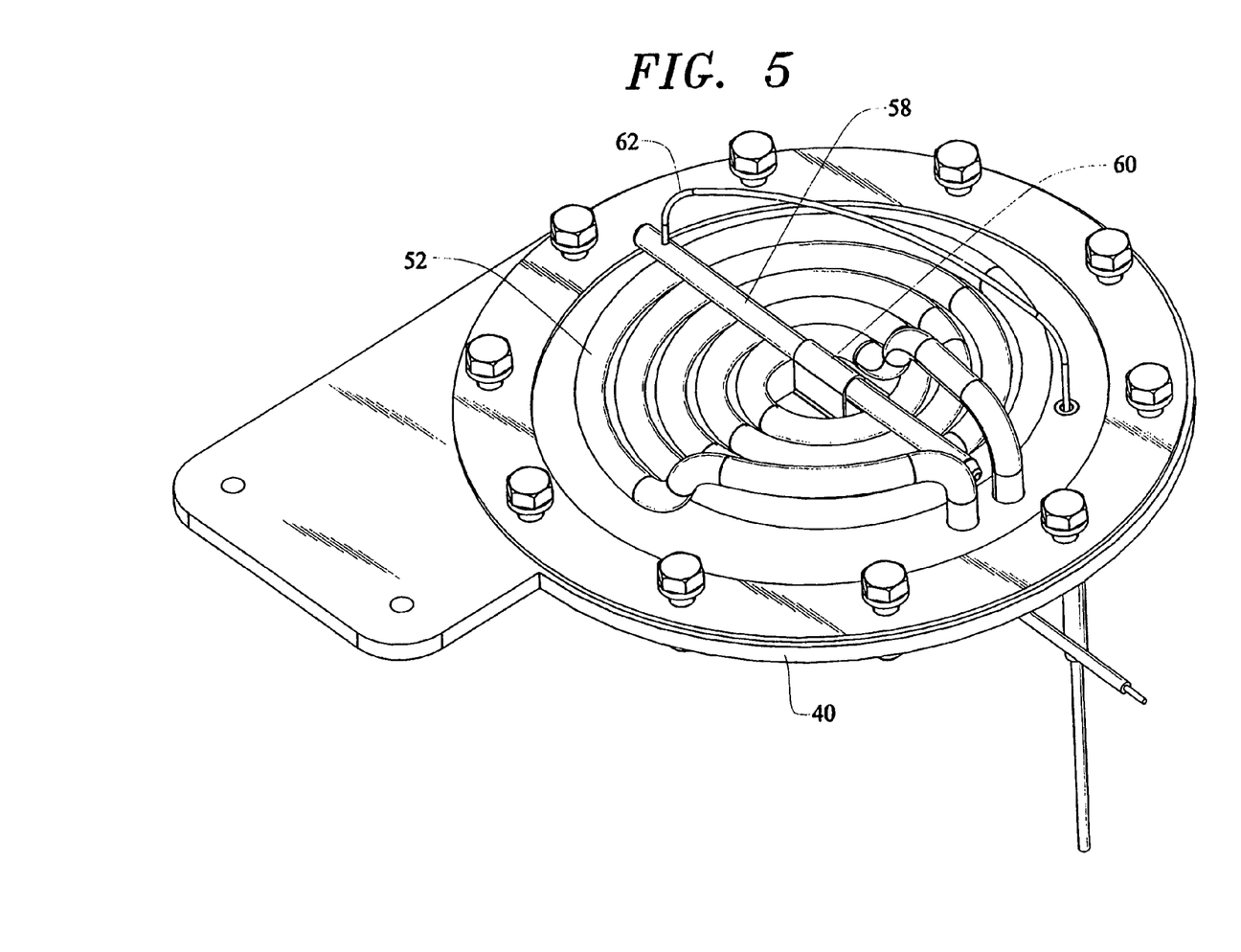
FIG. 5 is a perspective view of the steam generator of FIG. 4 with the top removed.
Figure 6:
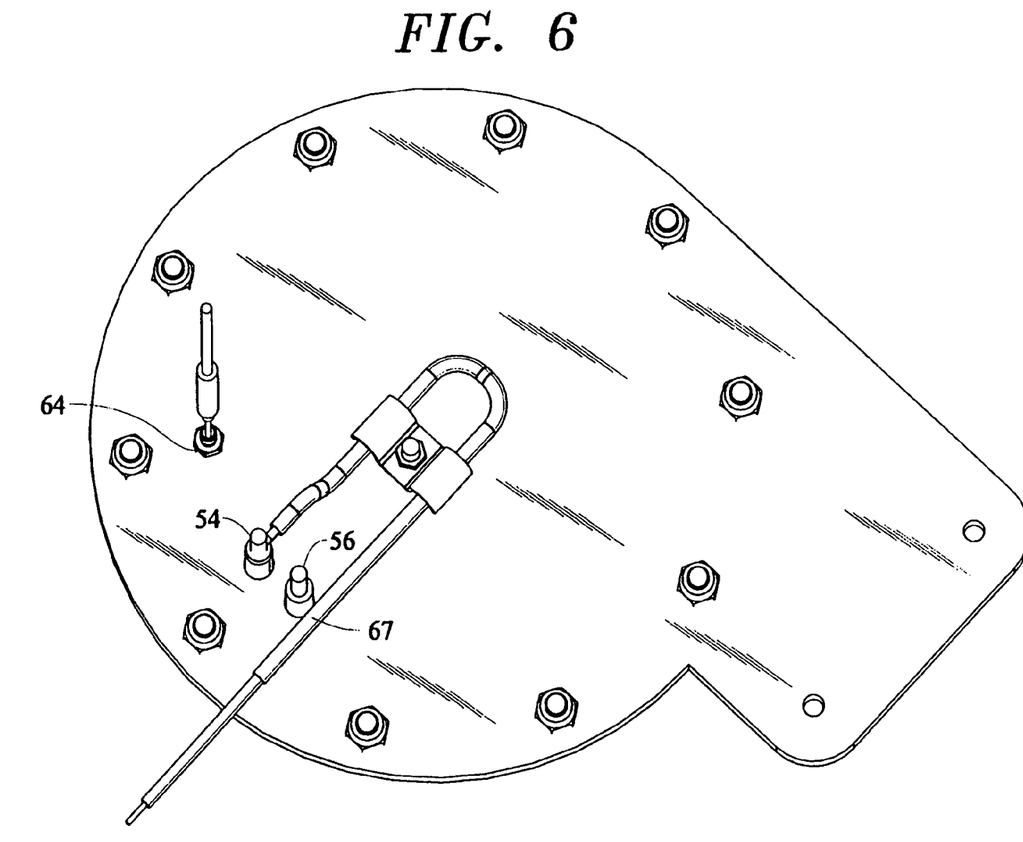
FIG. 6 is a bottom view of the steam generator of FIG. 4.

A preferred steam generator for use with the invention is shown in FIGS. 4 through 6. FIG. 4 shows a preferred steam generator embodiment, which comprises two parts, an upper deep drawn cap 38 and a lower stainless steel base plate 40. The two parts of the steam generator are connected together using a radial pattern of bolts 42 and nuts 44 with a gasket 46 between the two parts. This allows ease of disassembly of the steam generator for service purposes. The steam generated is conducted to the system through an outlet 48 on the cap. A conventional pressure relief valve 50 is installed on the cap as a safety device to prevent catastrophic failure of the steam generator.

FIG. 5 shows the base plate sub-assembly. A spiral heating element 52 is mounted on the base plate 40 and includes two terminals 54 and 56, which extend downwards through the plate. The terminals are secured to the base plate 40 by conventional means, such as by welding, to ensure that no leakage occurs at the interface with the plate. The coiled portion of the heating element 52 is mounted to the base plate such that it is free to move outward and upward, thus avoiding undue stresses caused by thermal expansion or contraction of the element. This is accomplished by fastening a rod 58, made of stainless steel or similar material, to the base plate by a central clamp 60, which is in turn fastened to the base plate by spot welding. The rod extends across the heating element and holds it to the base plate to ensure that no gap exists between the bottom of the heating element and the top of the base plate. This prevents the trapping of water or steam between the heating element and the plate and yet allows the rod to flex together with the heating element due to thermal expansion. A thermocouple 62 is inserted through the bottom of the base plate and is fastened to it by a compression fitting 64 (see FIG. 6). The temperature-sensing end of the thermocouple is fastened to the heating element by conventional means, such as by soldering. A thermal fuse 67, or a thermal switch, is mounted at the bottom of the base plate to cause a thermal cut-off if the heating element overheats.

In the preferred embodiment, the steam generator is mounted on the armature by conventional means such that the heating coil is tilted with respect to the horizontal. This creates a small region of the heating element that is exceptionally sensitive to a change in the water level inside the steam generator. As the water level decreases in the tilted steam generator due to steam generation, the region of the heating element that is at a slightly higher elevation will be exposed first, thus causing the temperature at that region of the heating element to surge when first exposed because at that point the remainder of the coil remains covered with water. Thus, placing the thermocouple 62 in that region of the heating element increases the response speed of the system's controller, thereby allowing water to be pumped into the steam generator on-demand.

Figure 7A:
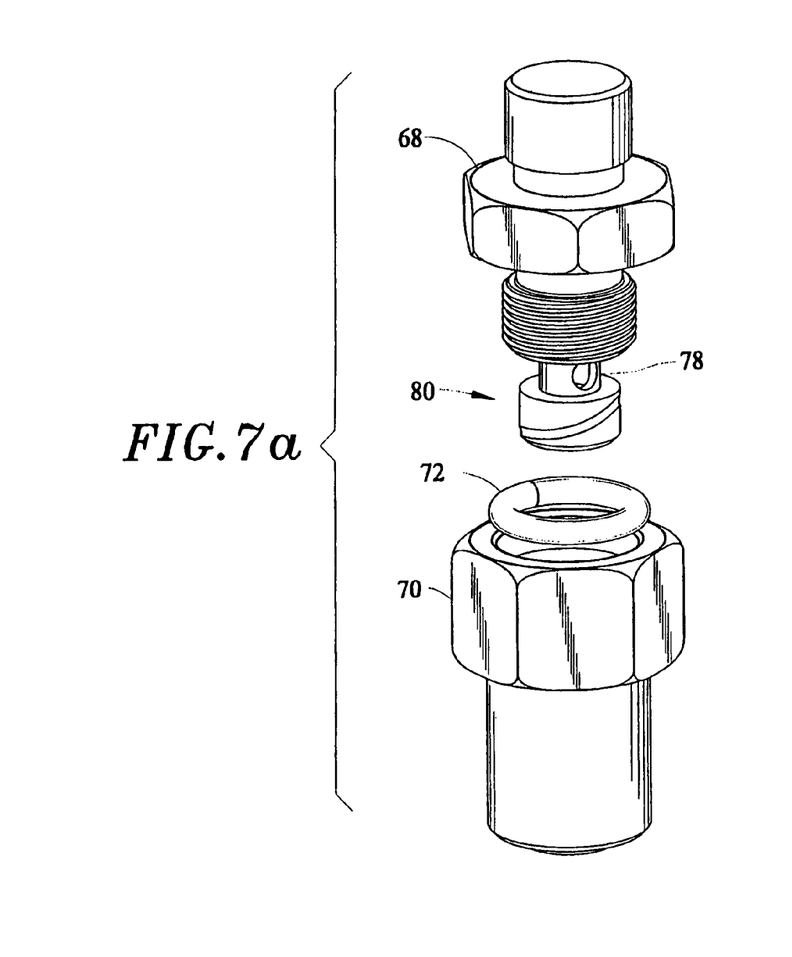
FIG. 7a is an exploded view of a preferred nozzle for the steam generator of FIG. 4.
Figure 7B:
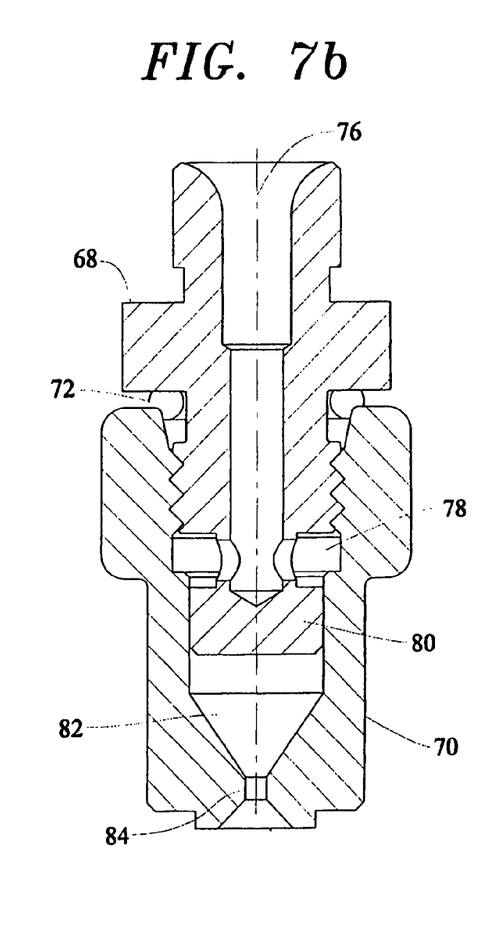

To facilitate steam generation, a spray nozzle 66, located at the top center of the steam generator, atomizes the inlet water. The spray nozzle breaks the water droplets into a mist, thereby increasing the total surface area of the water and reducing the time required to bring the fluid to the state of saturated steam. FIGS. 7a and 7b show a preferred spray nozzle embodiment composed of an accelerator fitting 68, which is threaded into a nozzle fitting 70 with an O-ring seal 72 placed therebetween to prevent leakage. Water is supplied under pressure from a pump 74 (see FIG. 8) to the inlet 76 of the accelerator fitting and travels downward through a crosshole 78 and thence into a downward-spiral acme threaded channel 80. A similarly spiral channel can be conceived in other embodiments of this design. The water travels downwards in a spiral trajectory, gaining angular momentum and accelerating and finally exits into a conical reservoir 82 leading into a small orifice 84 in the nozzle fitting 70. The sudden expansion upon exiting the orifice, together with the centrifugal force causes the water to spread out in the desired conical spray pattern, covering a substantial portion of the heating element upon contact. This spray pattern greatly facilitates the steam generation and at the same time provides uniform cooling of the heating element, thereby reducing the induced thermal stresses in the heating element. The orifice size of the spray nozzle is designed to prevent clogging of the nozzle, which could lead to cycle interruptions.

Figure 8:
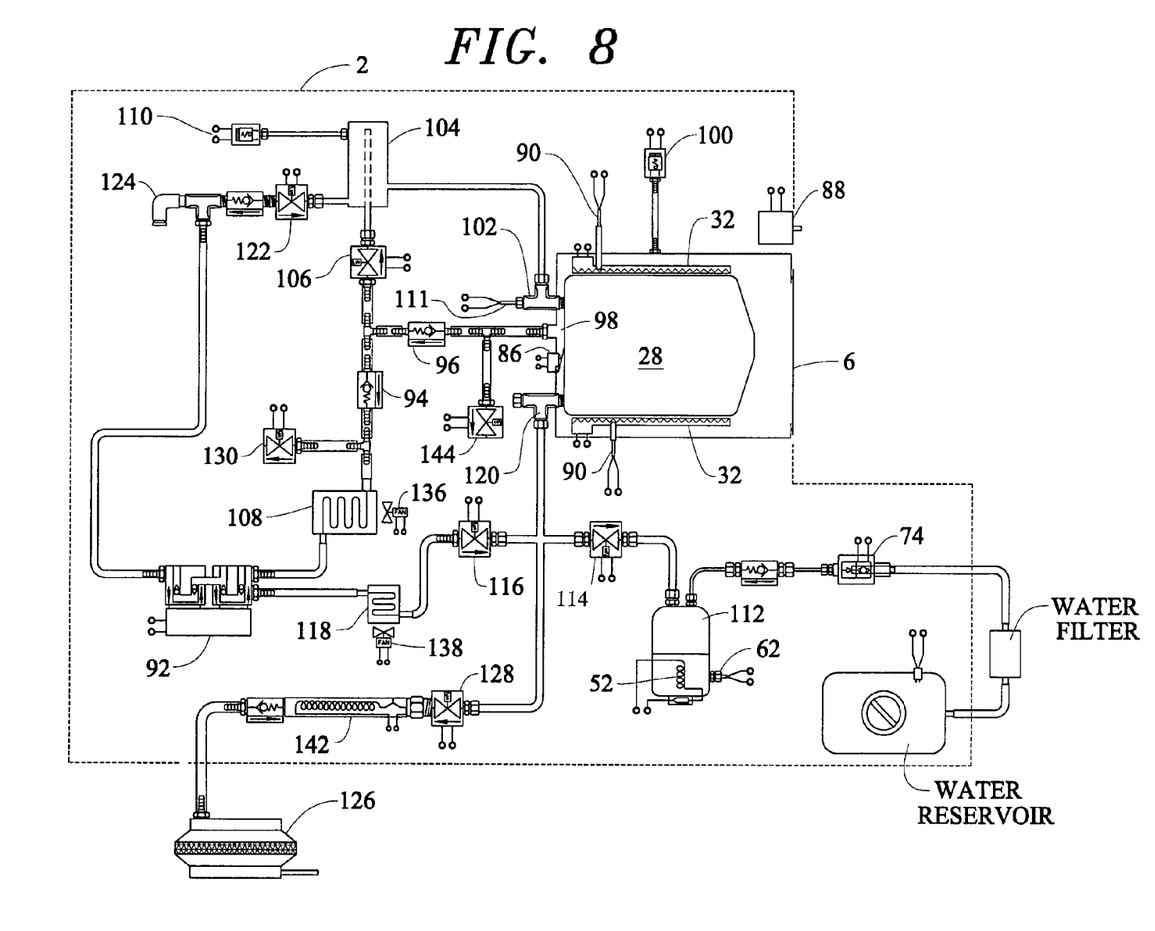
FIG. 8 is a schematic showing the elements and interconnections of the sterilizer of FIG. 1.
Figure 9:
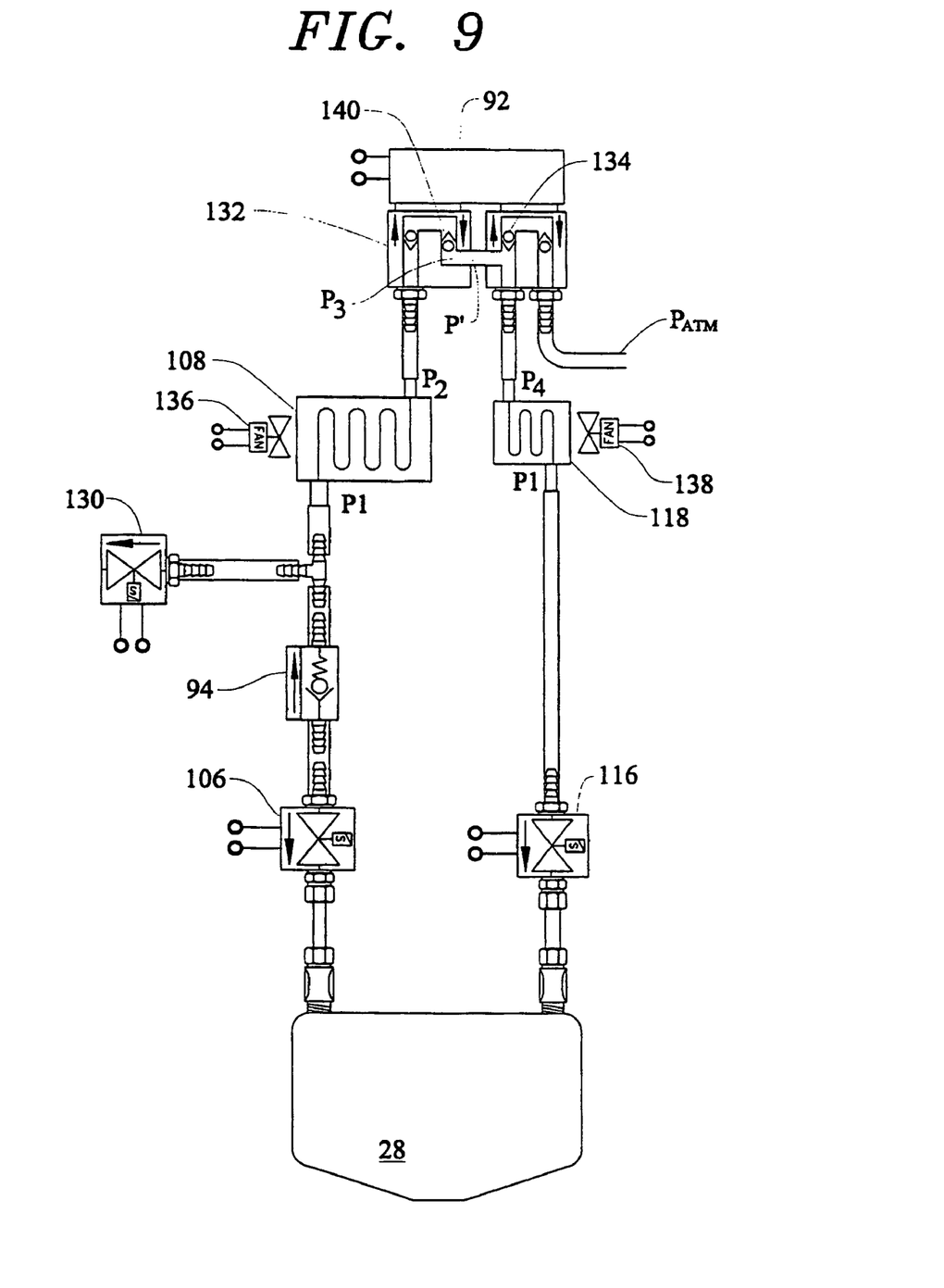
FIG. 9 is a schematic showing a vacuum draw with steam using dual heat exchangers.

The operation of the system will now be described in connection with FIGS. 8 and 9. FIG. 8 schematically illustrates the interconnection of various elements to provide a sterilizer system in accordance with the invention. FIG. 9 is a schematic showing only a functional part of the system shown in FIG. 8 during a steam vacuum draw. The process to be described carries out a sterilization cycle that is presently prescribed, and it will be appreciated that the structure described could be applied to other cycles and that the principles of the process could be applied to other processes.

With reference to FIG. 8, the sterilizing cycle begins when a cassette 28 is fully inserted into the cavity 4 and the door 6 closed. Insertion of the cassette is detected by a magnetically-operated reed switch 86 located at the end of the cavity, and closing the door fully is detected by a door switch 88, the closing of these switches resulting in activation of control circuitry that controls operation of the sterilizing cycle. When inserted, the cassette is also connected to the valve system to be described by probes that engage couplings on the cassette.

After the cassette has been fully inserted, the heating plates 32 are activated, which heats the cassette and increases the pressure inside the cassette. The distance between the upper and lower heating plates is preferably greater than the height of a cool cassette to allow easy insertion of the cassette, and expansion of the cassette results in full engagement of the cassette with the upper and lower heating plates. As noted above, the cavity also includes isolation plates, which engage the sides and rear of the cassette when fully inserted.

The heating plates may be thermally isolated from the armature to increase the heating efficiency, and the temperature of the heating plates is monitored by thermocouples 90. The temperature of the heating plates is controlled so that it remains within a few degrees of the sterilization temperature required for the particular instruments to be sterilized. Controlling the temperature of the cassette prevents condensation of steam on the interior of the cassette, on the one hand, and damage to the articles being sterilized by overheating, on the other.

The cassette must be filled with saturated steam during the sterilization stage, and the air in the cassette must first be removed. Because the cassette is made of relatively thin material, which cannot withstand the forces created by a vacuum, the cavity 4 surrounding the cassette is evacuated at the same time as is the cassette, whereby the pressure difference applied to the cassette is very small. In accordance with the preferred operation of the sterilizer, air is removed by a two-stage vacuum pump 92 after the temperature of the cassette is close to the sterilizing temperature. This vacuum pump is connected to the system by suitable tubing, such as Norprene®. When activated, the vacuum pump draws air from the cavity through check valves 94 and 96 and a fitting 98, which is attached to the back plate 24 and communicates with the cavity through opening 30. It will be appreciated that this arrangement ensures application of vacuum to the cavity whenever vacuum is applied to the cassette, to preclude collapse of the cassette.

Withdrawal of air from the cavity surrounding the cassette allows the cassette to be less expensive, as it need not have the strength required to withstand the forces resulting from vacuum pressures. This does add some time to the cycle because of the additional air that must be withdrawn from the cavity, but the additional time is minimized by conforming the shape of the cavity to the shape of the cassette, whereby the volume of air to be removed from the cavity with the cassette present is very small. Pressure in the cavity is preferably detected by sensor 100.

The vacuum pump 92 is connected to the cassette in two ways. First, the pump is connected to an outlet port of the cassette by a probe 102 when the cassette is fully inserted, as described in the mentioned Canadian patent application. The probe is connected to the vacuum pump via a water separator 104, a vacuum valve 106, and a regular heat exchanger 108. Thus, when the vacuum pump activated and the vacuum valve open, the vacuum pump will evacuate the cassette. The outlet port is also designed to withdraw condensate from the cassette, which is removed by the water separator 104. A pressure transducer 110 is provided to measure the pressure in the cassette, and a thermocouple 111 measures the temperature in the cassette.

The above arrangement allows detection of leaks in the cassette, the probe seal, and the vacuum valve 106 by evacuating the cavity while vacuum valve 106 is closed. Thus, the vacuum draw preferably begins with connection of the operating vacuum pump to the cavity alone. If no leaks are detected, the steam generator valve 114 and the valve 116 are opened to remove air from the steam generator 112, the structure of which was described in connection with FIGS. 4-6, and the cassette 128. This action ensures also that air is evacuated from the smaller heat exchanger 118, the regular heat exchanger 108, and the associated tubing.

The vacuum valve 106 is then opened to withdraw air from the cassette. Even at low vacuum, some air will remain after the first evacuation. Accordingly, when the vacuum level reaches the target, a second air removal procedure is done.

The second air removal procedure, with steam, is initiated by supplying steam to the cassette by first activating the steam generator 112 and then opening the steam generator valve 114 to allow steam to flow into the cassette through steam inlet 120. At this time, the vacuum valve is closed. As the steam fills the cassette and the voids in the instruments being sterilized, the pressure in the cassette increases. The cassette at this time is filled mostly with steam, but also with a small residual amount of air. The air is denser than the saturated steam, and when the pressure in the cassette increases to be just above atmospheric, exhaust valve 122 is opened to allow the steam to push the remaining air through outlet 124 to the atmosphere. The valve 122 is then closed again when the cassette pressure falls to atmospheric.

After the first vacuum draw and first vacuum-relief-with-steam phases of the sterilization cycle, most of the air has been removed from the system. The system is then almost entirely filled with saturated steam, and subsequent vacuum draws by the vacuum pump will no longer be effective due to the fact that there is no substantial pressure gradient across the pump to assist the flow.

The conventional means of creating a vacuum draw under the above condition is by means of a heat exchanger. As steam passes through the heat exchanger, it changes phase from the vapor state to the liquid state, thus greatly reducing the volume occupied within the system. This reduction in volume, in turn, creates a negative pressure gradient, or vacuum, within the system, which facilitates the vacuum draw.

To decrease the overall cycle time the invention provides dual heat-exchanger evacuation lines, each of which is connected to the cassette as illustrated in FIG. 9. The first of these evacuation lines includes vacuum valve 106, check valve 94, and a first, regular, heat exchanger 108. The second line includes second vacuum valve 116 and second, smaller, heat exchanger 118. The first and second evacuation lines operate according to different parameters while cooperating with each other to shorten the vacuum draw time. For example, the regular heat exchanger may be twice the size of the smaller one. It will be appreciated that the vacuum pump 92 can be a standard two stage pump modified to provide a second inlet to the second stage as shown. The preferred pump to be so modified includes interior check valves between the stages.

Operation of the dual-heat-exchanger-evacuation line in the vacuum draw is as follows. First, the system is effectively reduced to the formation illustrated in FIG. 9 by closing the steam generator valve 114, the air intake valve 128, and the exhaust valve 122 (see FIG. 8). This isolates the steam generator 112, air filter 126, armature cavity 4, and exhaust 124 from the system. Then the two-stage vacuum pump 92 is activated with the bleed valve 130 opened only momentarily to allow atmospheric air into the intake path of the vacuum pump, but not into the cassette. This action relieves any vacuum that may still exist within the two lines and allows the pump to begin operation. It will be appreciated that the pump could not begin to operate if a vacuum persisted in the lines. Once the vacuum pump is in operation, both the vacuum valve 106 and the second vacuum valve 116 are opened to connect the two lines to the cassette 28, thereby withdrawing steam from it. The steam, with pressure P1, will exit the cassette through both valves simultaneously and move toward the vacuum pump inlets 132 and 134.

Steam flowing into regular heat exchanger 108 is cooled by air circulated by cooling fan 136 and condenses. This creates a negative pressure P2 at the exit of the regular heat exchanger 108, where P2<P1. The steam/water mixture with pressure P2 enters the first stage of the two-stage vacuum pump 92 and exits the first stage pump at a slightly higher pressure P3 due to the pumping action.

The steam passing through the smaller heat exchanger 118, which is cooled by air circulated by a cooling fan 138, also condenses. The negative pressure created by this condensation reduces the pressure of the gas exiting the second heat exchanger to P4, where P4<P1. Pressure P4 is greater than P2 because the amount of condensation, and, hence, the pressure drop, taking place in the smaller heat exchanger is less than that taking place in the larger heat exchanger. Pressure P4 is also higher than P3 since the pressure increase due to the first-stage pumping action of the vacuum pump is relatively small.

The steam/water mixture with pressure P3 merges with the steam/water mixture with pressure P4 exiting from the second heat exchanger, resulting in a pressure P', where P'>P3. The exit check valve 140 of the first stage prevents the higher-pressure steam/water mixture from re-entering the first stage pump. Pressure P' creates a larger pressure gradient (P'>Patm) across the second stage vacuum pump, thereby facilitating the second-stage vacuum draw and increasing the rate of overall vacuum draw. The introduction of the second heat exchange line thus enables a faster pressure drop due to phase change from steam to water via condensation and at the same time maintains a large pressure gradient across the second stage of the vacuum pump to enable faster removal of the steam/water mixture by the vacuum pump.

It will be appreciated that the dual heat exchange evacuation line illustrated in FIG. 9 balances the need to evacuate steam rapidly with the need to remove the water from the system by using some of the potential energy reflected in the pressure remaining in the system to assist in removal of the water. The result is that a single vacuum pump can be used more efficiently, which is important in a desk-top system.

After the second vacuum draw, the pressure and temperature inside the cassette are increased to the levels required for sterilization. These parameters are mandated by regulation and may vary from country to country. Thus, the operation of the described apparatus may be varied to accommodate these standards.

Pressurization is accomplished by activating the steam generator 112 to produce steam and opening the steam generator valve 114. Steam flows through steam inlet 120 into the cassette, which purges any steam then in the cassette. When the predetermined pressure level required for sterilization is reached, the sterilization cycle begins.

The length of the sterilization cycle depends on the applicable standard. During sterilization, the correlation between the pressure of the steam and its temperature is closely monitored by the control system. Control of the sterilization pressure is preferably achieved by cyclically switching the power to the heating element in the steam generator on and off in response to the temperature sensed by the thermocouple 62.

Steam is generated on demand by pumping water into the steam generator when the temperature of the heating coil 52 ($dt_{on}$), sensed by the thermocouple 62, increases to a predetermined temperature. As noted above, because the heating coil is tilted, a small, upper portion of the heating coil will be exposed first as the water level in the steam generator decreases, and the temperature of that portion will increase rapidly to provide a sensitive measure of the state of the steam generator. Pumping is stopped when the temperature of the heating coil decreases to a predetermined threshold ($dt_{off}$).

The cassette is maintained at the prescribed temperature and pressure for the prescribed period of time required to sterilize the instruments. Then, the exhaust valve 122 is opened and controlled to release the pressure in the cassette at the rate specified by the relevant standards. The exhaust water is also collected in an exhaust water container (not shown). At this time, the heating plates 32 are activated and maintained above the boiling point of water for the pressure inside the cassette, to prevent formation of water in the cassette as the pressure decreases.

Then the cassette is prepared for removal and storage of the sterilized instruments by first ensuring that no steam remains in the cassette. This is done by first opening the bleed valve 130 momentarily and activating the vacuum pump 92. Then the bleed valve is closed and the vacuum valve 106 opened to draw the remaining steam out of the cassette. During this step, the valve 116 remains closed, and the heating plates 32 remain activated to ensure that no water forms in the cassette. Following removal of the steam, the air valve 128 is opened, which draws air through filter 126 and into the cassette. An optional heater 142 heats this air to avoid condensation, and the air cools the sterilized instruments for a period of time that depends on the sterilization load.

The sterilization cycle is then complete, and the armature valve 144 is opened to allow the cavity pressure to return to atmospheric. Then, the door 6 may be opened and the cassette removed. Preferably, valves on the cassette close as they are detached from the probes in the cavity, whereby the cassette remains isolated from the ambient.

It will be appreciated that various electronic components and methods may be employed to implement the described procedures. In the preferred embodiment, an input/output board and a logic board are provided to read the various temperatures and pressures, to control the valves and pumps as described, and to display relevant information, such as a graph showing the progress of the sterilization cycle.

Modifications within the scope of the appended claims will be apparent to those of skill in the art.

We claim:

1. A sterilizer comprising:
    an armature forming a pressure tight cavity adapted to receive a removable cassette,
    a steam generator having an outlet connected to a steam inlet, said steam inlet being adapted to be connected to said cassette, and
    a vacuum pump operatively connected to a fitting in fluid communication with said pressure tight cavity to withdraw air from said pressure tight cavity alone, and said vacuum pump operatively connected to a probe configured to be connected to an outlet port of said cassette to withdraw air or steam from said cassette at the same time that air or steam is withdrawn from said pressure tight cavity.

2. A sterilizer according to claim 1 wherein said armature comprises an extrusion having an inner wall, an outer wall, and a plurality of webs connecting said inner and outer walls.

3. A sterilizer according to claim 2 wherein said extrusion is of aluminum.

4. A sterilizer according to claim 1 further comprising at least one heating plate in said cavity arranged to contact said cassette when in said cavity.

5. A sterilizer according to claim 1 wherein said steam generator comprises a plate having an electric heating coil having one side secured to said plate by a rod that is secured to said plate and extends across an opposed surface of the heating coil.

6. A sterilizer according to claim 5 wherein said steam generator comprises a thermocouple attached to one part of said heating coil.

7. A sterilizer according to claim 6 wherein said steam generator is oriented such that when in use said heating coil is tilted with respect to the horizontal.

8. A sterilizer according to claim 5 wherein said steam generator includes an inlet nozzle arranged to spray droplets onto said heating element.

9. A sterilizer according to claim 1 wherein said vacuum pump is connected to said outlet of said steam generator.

10. A sterilizer according to claim 1 wherein said vacuum pump is a two-stage vacuum pump and said sterilizer further comprises a first heat exchanger and first control valve connected between the inlet of a first stage of said vacuum pump and said probe, and a second heat exchanger and second control valve connected between an inlet to the second stage of said vacuum pump and said steam inlet.

11. A sterilizer according to claim 10 wherein said first heat exchanger is larger than said second heat exchanger.

12. A method for sterilizing instruments comprising the steps of:
    providing an armature having a pressure tight cavity for receiving a sterilizing cassette that is sealed against fluid communication with said pressure tight cavity after it has been placed in said cavity, placing said sterilizing cassette in said pressure tight cavity, and withdrawing air from both said sterilizing cassette and said pressure tight cavity at the same time.

13. A method according to claim 12 further comprising the step of supplying steam to said sterilizing cassette and then withdrawing said steam by drawing said steam through first and second heat exchangers arranged in parallel, wherein said first heat exchanger is larger than said second heat exchanger.

14. A method according to claim 13 further comprising withdrawing the outputs of said first and second heat exchangers with a two-stage vacuum pump having an inlet to a first stage connected to the output of said first heat exchanger and an inlet to a second stage connected to the output of said second heat exchanger.

15. A sterilizer comprising:
    an armature forming a cavity adapted to receive a removable sterilizing cassette,
    a steam generator having an outlet connected to a steam inlet, said steam inlet being adapted to be connected to said removable sterilizing cassette, and a vacuum pump having an inlet connected to a probe to be connected to an outlet port of said removable sterilizing cassette wherein said armature comprises an extrusion having an inner wall, an outer wall, and a plurality of webs connecting said inner and outer walls.

16. A sterilizer according to claim 15 wherein said extrusion is of aluminum.

17. A method for sterilizing instruments comprising the steps of: providing an armature having a cavity for receiving a removable sterilizing cassette, withdrawing air from both said removable sterilizing cassette and said cavity, supplying steam to said removable sterilizing cassette and then withdrawing said steam by drawing said steam through first and second heat exchangers arranged in parallel, wherein said first heat exchanger is larger than said second heat exchanger.

18. A method according to claim 17 further comprising withdrawing the outputs of said first and second heat exchangers with a two-stage vacuum pump having an inlet to a first stage connected to the output of said first heat exchanger and an inlet to a second stage connected to the output of said second heat exchanger.

19. A sterilizer according to claim 1 in combination with a sterilizing cassette that is sealed against fluid communication with said pressure tight cavity when it is in an operational position in said cavity.

* * * * *